United States Patent
Gesswein et al.

(10) Patent No.: US 6,423,026 B1
(45) Date of Patent: Jul. 23, 2002

(54) CATHETER STYLET

(75) Inventors: Douglas H. Gesswein, Temecula;
Kathleen L. Stillman, Murrietta;
Pablito M. Buan, Temecula, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/458,360

(22) Filed: Dec. 9, 1999

(51) Int. Cl.[7] .............................................. A61B 17/20
(52) U.S. Cl. ........................................................ 604/22
(58) Field of Search ......................... 604/22, 264, 523, 604/524, 525, 526, 527, 528, 529, 530

(56) References Cited

U.S. PATENT DOCUMENTS

| 5,397,301 A | 3/1995 | Pflueger et al. |
| 5,427,118 A | 6/1995 | Nita et al. |
| 5,542,917 A | 8/1996 | Nita et al. |
| 5,989,208 A * | 11/1999 | Nita ............................ 600/467 |
| 5,989,275 A * | 11/1999 | Estabrook et al. ............. 604/22 |
| 6,083,232 A * | 7/2000 | Cox ............................... 601/2 |
| 6,296,620 B1 * | 10/2001 | Gesswein et al. .............. 604/22 |

* cited by examiner

*Primary Examiner*—Teresa Walberg
*Assistant Examiner*—Vinod Patel
(74) *Attorney, Agent, or Firm*—Fulwider Patton Lee & Utecht, LLP

(57) ABSTRACT

The present invention is directed to a catheter style for shaping an ultrasound catheter for delivering ultrasonic energy to a treatment location within a patient's body. The stylet has sufficient stiffness, with a shaped distal end, to bring about the desired deflection at a catheter distal end to negotiate the catheter through tortuous anatomy during treatment.

21 Claims, 4 Drawing Sheets

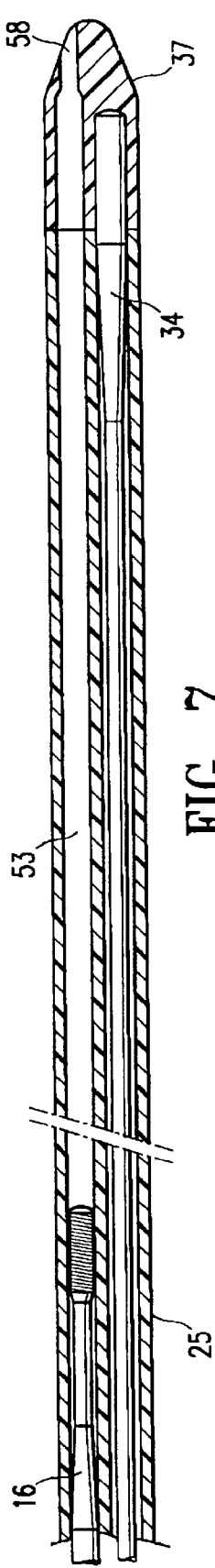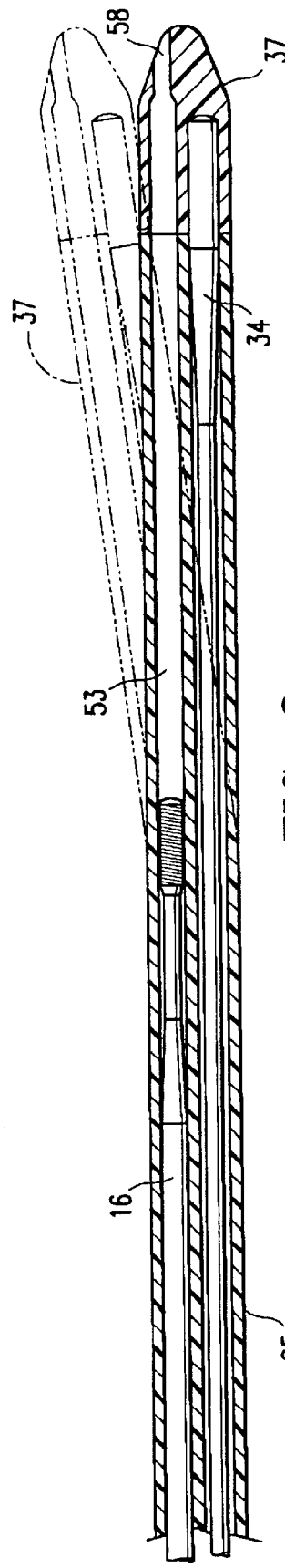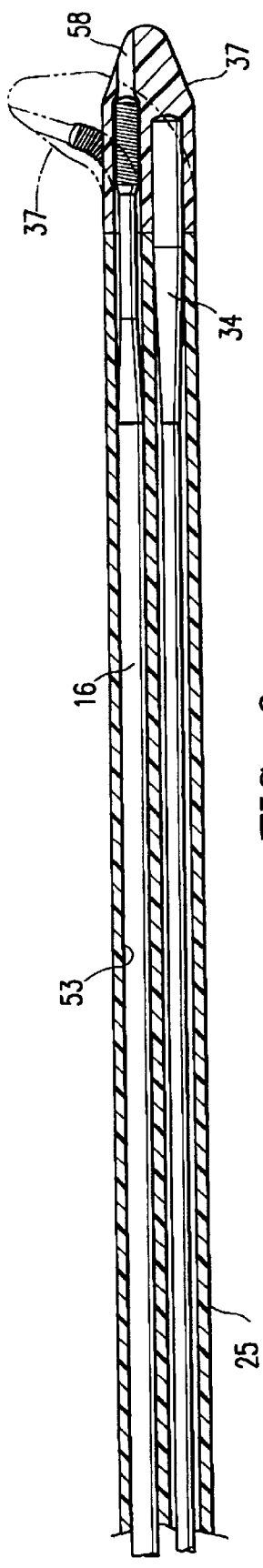

CATHETER STYLET

FIELD OF INVENTION

This invention relates generally to medical devices and more particularly to ultrasonic angioplasty catheters for effecting ultrasonic ablation of occlusive intravascular lesions.

BACKGROUND OF THE INVENTION

Ultrasound transmitting catheters have been utilized to successfully ablate various types of obstructions from blood vessels of humans and animals. Additionally, ultrasound transmitting catheters may be utilized to deliver ultrasonic energy to mammalian blood vessels for the purpose of preventing or reversing vasospasm, as described in U.S. Pat. No. 5,324,255 (Passafaro, et al.).

Particular success has been observed in ablation of atherosclerotic plaque or thromboembolic obstructions from peripheral blood vessels such as the femoral arteries. Successful applications of ultrasonic energy to smaller blood vessels, such as the coronary arteries, necessitates the use of ultrasound transmitting catheters which are sufficiently small and flexible to permit transluminal advancement of such catheters through the tortuous vasculature of the aortic arch and coronary tree. Accordingly, the safety and efficacy of removing obstructions from coronary arteries by way of ultrasound is largely dependent upon the size and flexibility of the ultrasound transmitting catheter(s) employed.

One particular type of ultrasound transmitting catheter which may be utilized to deliver therapeutic ultrasound to an intracorporeal treatment site comprises an elongate flexible catheter body having rigid distal tip or head member inserted into, and affixed thereto with at least one ultrasound transmission member extending longitudinally through the catheter body being coupled to the distal tip or head member, as described in U.S. Pat. No. 5,542,917 (Nita, et al.).

Although these devices are of merit, there still exists a need in the art for further invention, development and refinement of the previously known ultrasound catheters to provide catheters with improved maneuverability for advancing through the small and tight tortuous blood vessels, such as the coronaries arteries.

SUMMARY OF THE INVENTION

The present invention is directed to a catheter style for shaping an ultrasound catheter for delivering ultrasonic energy to a treatment location within a patient's body. The stylet of the present invention has proximal and distal portions with a distal end. The stylet distal end is sufficiently larger than a distal passage aperture of the ultrasound delivery catheter to maintain the stylet distal end within the ultrasound delivery catheter body at the distal end of the ultrasound delivery catheter. Additionally, the stylet has sufficient stiffness to bring about the desired deflection at the catheter distal end to negotiate the catheter through tortuous anatomy during treatment. Preferably, the distal end of the stylet has a predetermined shape, preferably in the shape of a curve to bring about the desired deflection at the distal end of the ultrasound delivery catheter.

In one embodiment, the stylet comprises an elongate core member having proximal and distal portions with a distal end. Additionally, a flexible body having a distal end is disposed about a section of the elongate core member distal portion. The flexible body is secured to the elongate core member a point proximal to the elongate core member distal end. The flexible body, may further include a plug at the distal end thereof. The plug has is sufficiently larger than a distal aperture of the catheter such that the distal end of the stylet is kept within the catheter body at the distal end of the catheter during treatment.

In operation, the stylet is inserted into the catheter body (before or after the catheter body has been inserted into the patient's body). The stylet is moved longitudinally within and with respect to the catheter body to bring about a desired deflection at the catheter distal end, allowing the catheter to be negotiated through tortuous anatomy. Thereafter, the stylet is removed from the catheter.

BRIEF DESCRIPTION OF THE DRAWINGS

FIG. 7 is a cross sectional view of the distal portion of the ultrasound delivery catheter of FIG. 5 with a portion of the catheter stylet of FIG. 2, disposed therein.

FIG. 8 is a longitudinal sectional view of the ultrasound delivery catheter and catheter stylet of FIG. 7, showing a longitudinal movement of the stylet within the ultrasound delivery catheter body to bring about a desired deflection at a distal end of the ultrasound delivery catheter.

FIG. 9 is a longitudinal sectional view of the ultrasound delivery catheter and catheter stylet of FIG. 8, with the catheter stylet being farther along toward the distal end of the ultrasound delivery catheter and effecting a greater deflection at the distal end thereof.

DETAILED DESCRIPTION OF THE INVENTION

Figure 1:
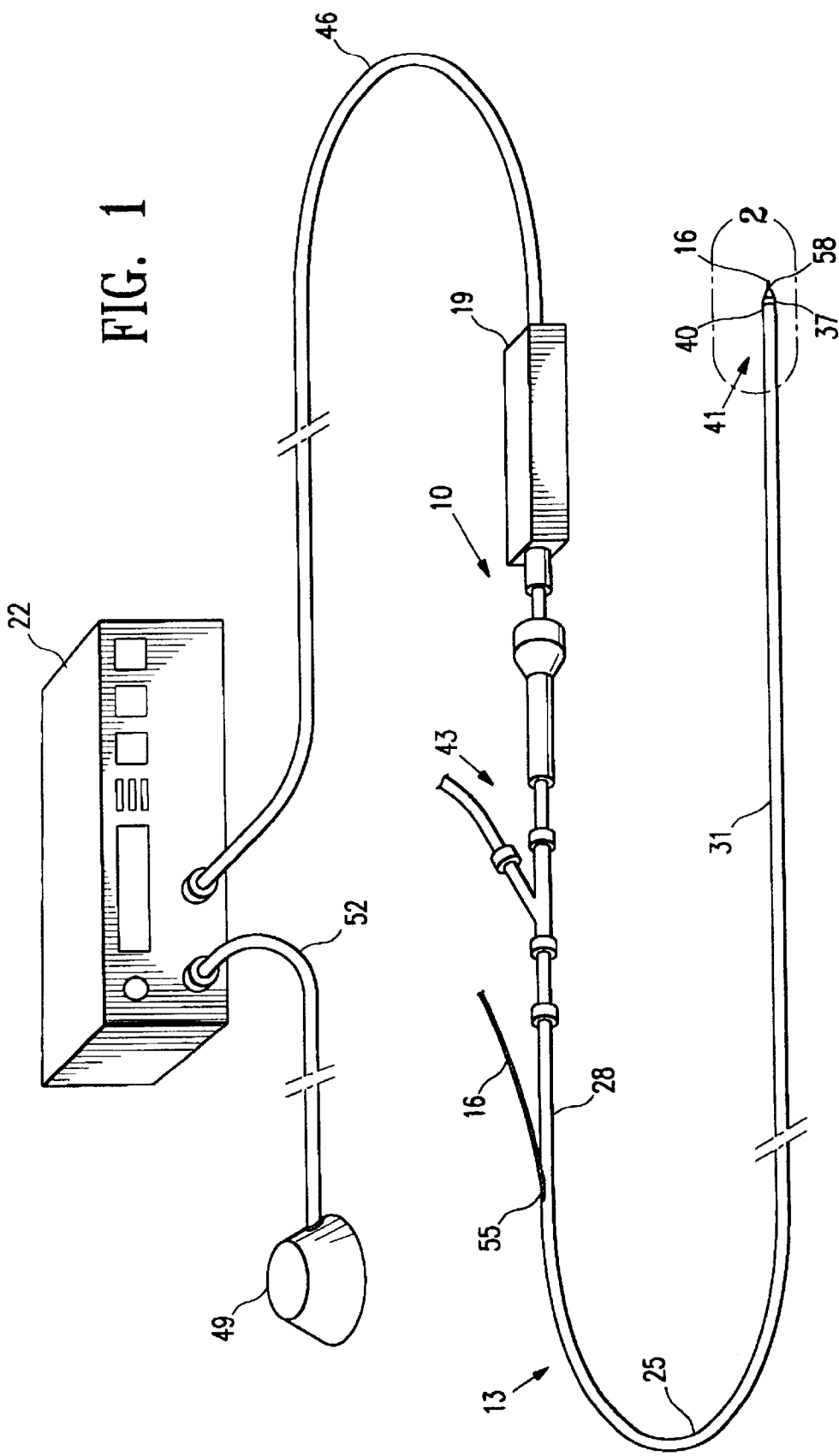
FIG. 1 is a general perspective view of an ultrasound delivering system including an ultrasound delivery catheter adaptable to receive a catheter stylet of the present invention.

FIG. 1 illustrates features of an ultrasound delivery system 10 including an ultrasound delivery catheter 13 adaptable to receive a catheter stylet 16, an ultrasound transducer 19, and an electrical signal generator 22.

The ultrasound delivery catheter 13 comprises an elongate pliable catheter body 25 having a proximal portion 28, a distal portion 31, and at least one ultrasound transmission member 34 (shown in FIG. 5) extending longitudinally therethrough. At a distal section 41 of the catheter 13, a distal tip member 37 is mounted on a distal end 40 of the pliable catheter body 25 and the elongate ultrasound transmission member 34 is connected to or in abutment with the distal tip member 37 so as to transmit ultrasonic vibration to the distal portion 31 of the catheter body 25. A proximal connector assembly 43 is positioned on a proximal portion 28 of the catheter body 25 and is configured and constructed to facilitate operative connection of an proximal end of the ultrasound transmission member 34 to the ultrasound transducer 19 such that ultrasonic energy may be transmitted by the ultrasound transmission member 34, from the ultrasound transducer 19 to the distal end 40 of the catheter 25.

The ultrasound transducer 19 is connected to the electrical signal generator 22 by way of cable 46. An on/off foot pedal switch 49 is connected to the electrical signal generator 22 by way of a cable 52. By such arrangement, the on/off foot pedal switch 49 may be depressed to cause the signal generator 22 to emit an electrical signal through cable 46 to ultrasound transducer 19. The ultrasound transducer 19 is operative to convert the electrical signal into ultrasound energy at a frequency, and in a pattern which, when transmitted to the distal end 40 of the catheter 13, will effect the intended therapeutic or ablative application.

The catheter 13 shown in FIG. 1 is a "monorail" or "rapid exchange" type of catheter wherein a guide wire lumen 53 (FIG. 5) extends longitudinally through a distal portion of the catheter body 25, between a first proximal guide wire passage aperture 55 formed in the side wall of the catheter body 25 and a second distal guide wire passage aperture 58 formed in the distal tip member 37 at the distal end 40 of the catheter body 25. By such an arrangement, the stylet 16 may be longitudinally advanced or retracted through the proximal aperture 55 and may be disposed adjacent to the outside of the proximal portion 28 of the catheter body 25.

It will be appreciated that, in an alternative to the "monorail" design shown in FIG. 1, the catheter 13 of the present invention may also be configured as an "over-the-wire" catheter wherein the guide wire lumen 53 extends longitudinally through the catheter body 25 and a guide wire entry/exit side arm (not shown) is formed on the proximal connector assembly 43 such that the guide wire or stylet 16 may be inserted through the entire length of the catheter 13, and is insertable/extractable through a side arm or aperture formed in the proximal connector assembly 43.

The proximal connector assembly 43 on the proximal end of the catheter 13 may be configured and constructed in many different ways to accomplish the desired function of operatively coupling the ultrasound transmission member 34 of the catheter 13 to the ultrasound transducer 19, such as that described in U.S. Pat. No. 5,542,917 (Nita, et al.), and incorporated herein by reference.

The connection of the proximal end of the ultrasound transmission member 34 to the ultrasound transducer 19 is accomplished through conventional means, such as that described in Nita, referenced above. =In many applications, it may be desirable for the catheter 13 to have optimal pliability or flexibility, especially in the distal portion of the catheter body 25, such that the catheter may be inserted into small or tortuous anatomical passageways without crimping of the catheter body or breakage/damage to the ultrasound transmission member 34. The ultrasound transmission member 34 spans the entire length of the catheter 13 adding to its stiffness, thus making it more difficult to maneuver through tortuous anatomy. To aid the catheter body 25 through tight anatomy and abrupt side branches the stylet 16 can be used to direct the catheter body 25 to the desired location. The stylet 16 will have such stiffness so as to influence the natural shaping of the catheter body 25 as it is moved through the anatomy. As the stylet 16 is pushed distally or retracted proximally in the catheter body 25, it alters the shape of the catheter body at its distal section 41, enabling it to negotiate the bends within the body more easily. Once the catheter has been positioned at the desired location within the body, the stylet 16 can be removed and replaced with a guidewire.

Figure 2:
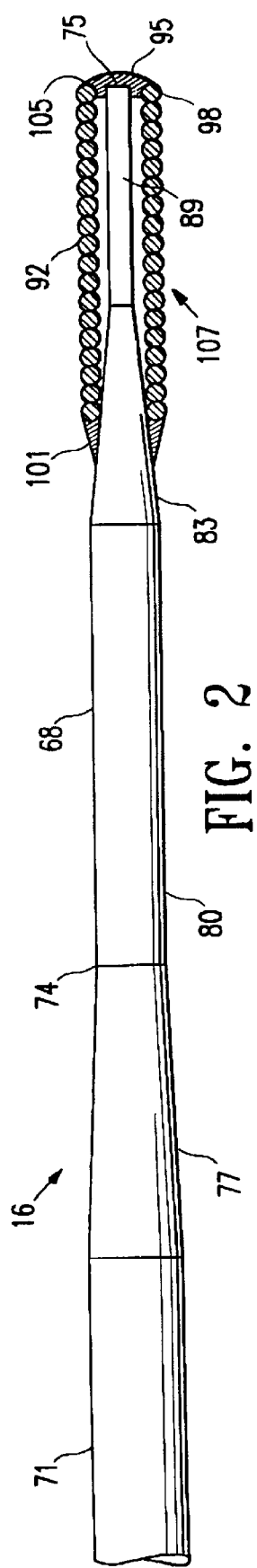
FIG. 2 is a side elevational view of the catheter stylet incorporating features of the invention.

FIG. 2 illustrates features of the catheter stylet 16 embodying the present invention in its straight configuration. The stylet 16 comprises an elongate core member 68 having proximal portion 71 and a relatively short distal portion 74 with a distal end 75. The distal portion 74 may have one or more tapered regions, such as 77, 80, and 83 becoming smaller in the distal direction. The core member 68 at its most distal section 89 may optionally be flattened.

A flexible body, such as a helical coil 92 may optionally be disposed about a portion of the distal portion 74 and has a rounded plug 95 on a distal end 98 thereof. The coil 92 is secured to the distal portion 74 at a proximal location 101 by a suitable solder. The coil 92 preferably covers the entire longitudinal dimension of the core member distal section 89 and extends proximally covering at least a portion of the tapered region 83.

The core member 68 at its largest cross sectional area (e.g., proximal portion 71) is sufficiently smaller than the internal diameter of the guide wire lumen 53 extending longitudinally through the catheter body 25. The stylet 16 at its distal end 105, is of sufficient transverse dimension such that when inserted into the catheter body 25, the stylet 16 will not exit the distal passage aperture 58. This can be achieved, for example, by appropriately sizing the rounded plug 95 of the coil member 92, or the distal end 75 of the core member 68 when a coil 92 is not used.

The stylet 16, is formed of one or more materials, such that the stylet 16 is sufficiently stiffer than the catheter body 25.

The core member 68 may be formed of one or more materials which exhibit super elasticity in the range of operating temperatures at which the stylet is employed, such as stainless steel. =The coil 92 is made of a material with sufficient stiffness to bring about the necessary deflection at the distal end 40 of the catheter body 25 enabling the catheter body 25 to negotiate the tortuous anatomy, such as stainless steel or an alloy of platinum/nickel. The Pt/Ni alloy, preferably, comprises from about 88 to about 92 atomic % platinum, preferably, from about 89 to about 91 atomic % platinum; with the balance nickel. The distal most section 107 of the stylet is formed of a radiopaque material as for example the Ni/Ti material of the coil 92.

Figure 3:
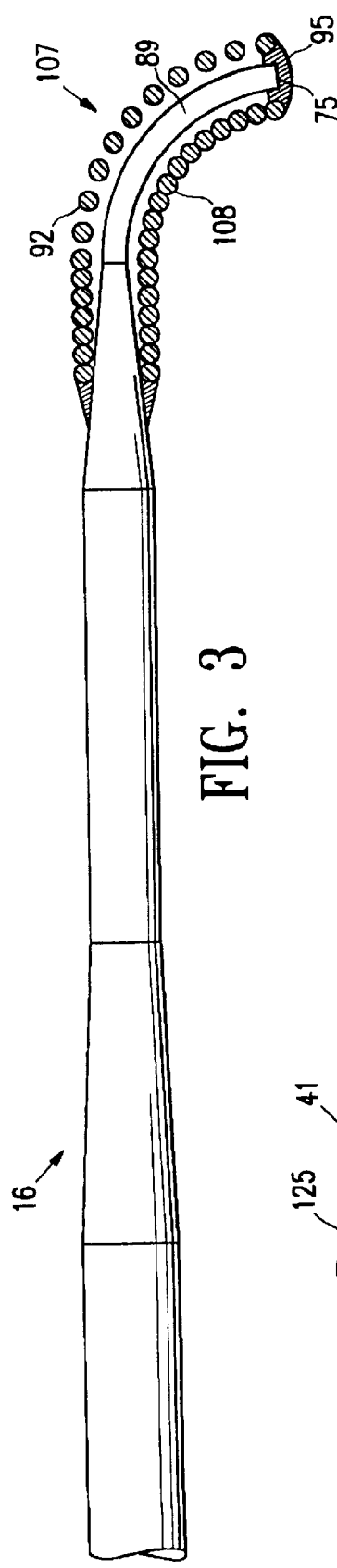
FIG. 3 is a side elevational view of the catheter stylet of FIG. 2 in its curved configuration.

As shown in FIG. 3, the stylet 16, at its most distal section 107 is preshaped to have a curve 108 in the range from about 900 to about 2700 with a radius of curvature ranging from about 0.25 to about 2 inches. The curve or bend 108 is formed within up to about 2 mm of the distal end 75 of the stylet, preferably within up to about 1 mm.

The stylet may further be coated with a lubricating agent such as Teflon™ or Hydrocoat™.

The distal tip member 37 of the catheter 13 may be configured and affixed to the distal end 40 of the catheter body 25 in different ways, such as those described in Nita, an example of which is described below.

Figure 4:
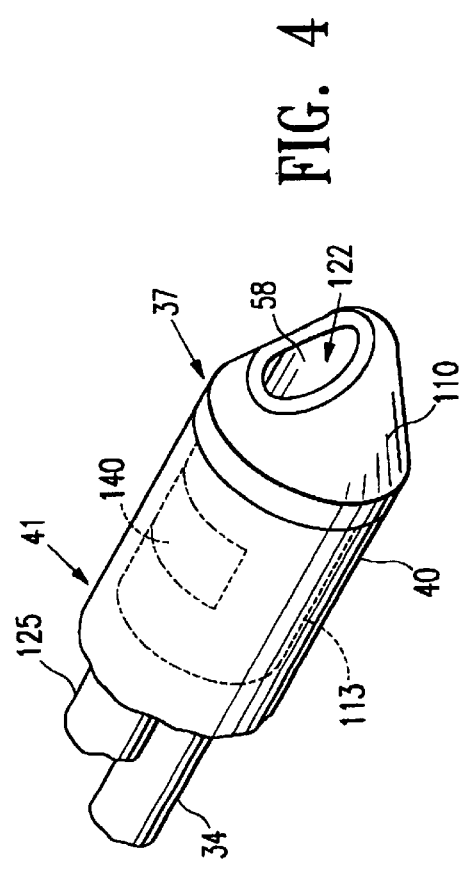
FIG. 4 is an enlarged perspective view of a distal section of the ultrasound delivery catheter of FIG. 1.
Figure 5:
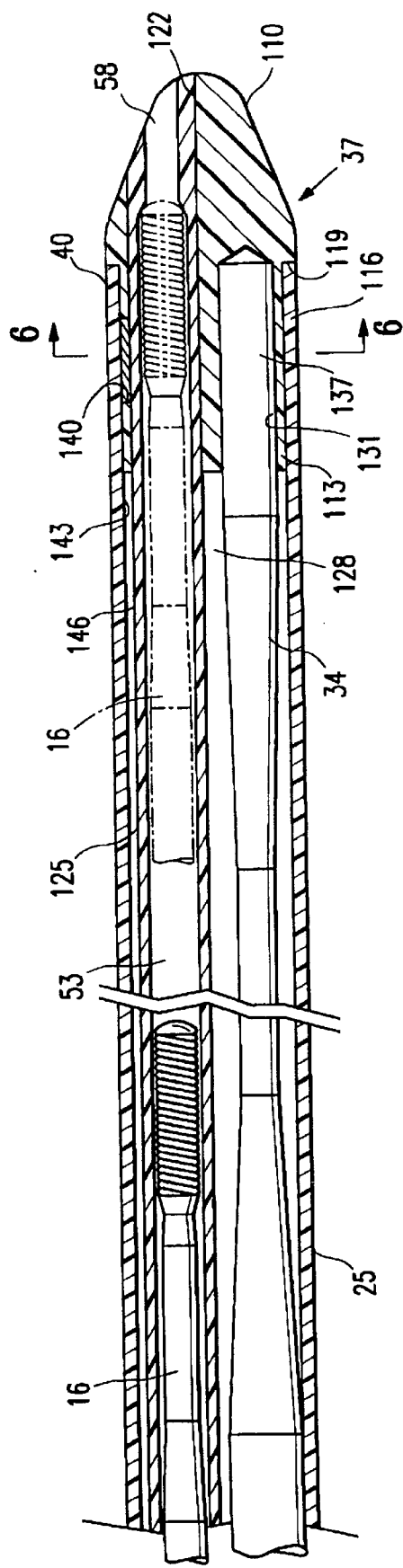
FIG. 5 is a longitudinal sectional view of the distal portion of the ultrasound delivery catheter of FIG. 4, with the catheter stylet position as it moves along the catheter lumen, shown in phantom.
Figure 6:
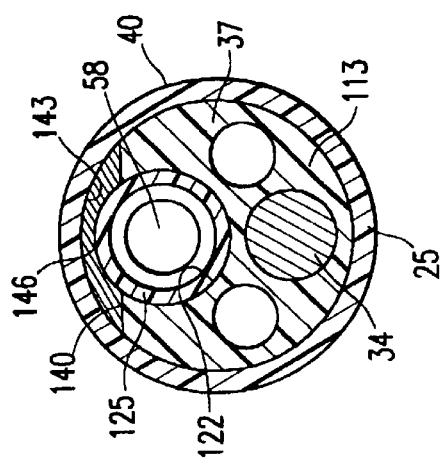
FIG. 6 is a cross sectional view of the distal portion of the ultrasound delivery catheter of FIG. 5 taken along line 6—6.

As shown in FIGS. 4, 5, and 6, the distal tip member 37 comprises a generally conical distal portion 110 and a smaller diameter, generally cylindrical, proximal portion 113. The generally cylindrical proximal portion 113 is sized to be insertable into the distal end 40 of the tubular catheter body 25 such that the distal tip 116 of the tubular catheter body 25 will abut against the annular shoulder 119 of the distal portion 110. A longitudinal guide wire passage bore 122 is formed eccentrically through the entire length of the distal tip member 37 such that a separate guide wire tube 125, defining the guide wire lumen 53, may be passed through the catheter lumen 128 and through the guide wire passage bore 122.

The distal end of the guide wire tube 125 is cut flush with the distal face of the distal portion 110 of the distal tip member 37, as shown. When so inserted, the guidewire tube 125 may be affixed or secured to the distal tip member 37 by heat sealing, adhesive or other suitable means.

Also, an ultrasound transmission member receiving bore 131 extends longitudinally into a proximal portion of the distal tip member 37, terminating in a conical or pointed blind end point 134. The ultrasound transmission member receiving bore 131 is formed eccentrically in the distal tip member 37, spaced apart from the location of the guidewire passage bore 122. The ultrasound transmission member receiving bore 131 is sized and configured to receive the distal-most portion of the ultrasound transmission member 34. In the embodiments shown, an extreme distal end 137 of the ultrasound transmission member 34 is advanced to a point where it abuts against the decreasing diameter of the blind conical end point 134 of the ultrasound transmission member receiving bore 131.

The ultrasound transmission member 34, the guidewire tube 125, and the catheter body 25 may be fixed or engaged to the distal tip member 37 by any suitable means, such as those described in Nita.

For example, as shown in FIG. 5, a three way bond is formed between the distal end 40 of the catheter body 25, the distal tip member 37 and the guidewire tube 125, by providing an adhesive passage aperture 140 in the proximal portion 113 of the distal tip member 37 such that a quantity of adhesive may be disposed within aperture 140, thereby bonding the inner surface 143 of the tubular catheter body 25 to the outer surface 146 of the guidewire tube 125, while adhesively locking or holding the distal tip member 37 in its desired position within the distal end 40 of the catheter body 25. The adhesive passage aperture 140 may be in the form of a single generally rectangular aperture formed in one side of the proximal portion 113 of the distal tip member 37, extending from the outer surface of the proximal portion 113, into the guidewire passage bore 122 formed therein. A quantity of adhesive may be initially disposed on the outer surface of the proximal portion 113 of the distal tip member 37 and/or within the confines of the aperture 140. Thereafter, the distal tip member 37 is inserted into the distal end 40 of the tubular catheter body 25, and the guidewire tube 125 is passed through the guidewire passage bore 58. The quantity of adhesive which resides or flows through aperture 140, upon curing, will form a three way adhesive bond between the inner surface of the catheter body 25, the proximal portion 113 of the distal tip member 37 and the outer surface of the guidewire tube 125. Such a three way bond serves to firmly hold the distal tip member 37 in its desired position while also preventing slippage or release of the guidewire tube 125. Again, as described above, distal end 105 of the stylet 16 (e.g., the rounded plug 95 of coil 92 or the distal end 75 of the core member 68) is of sufficient dimension such that when inserted into the catheter body 25, the stylet 16 will not exit the distal passage aperture 58.

In operation, the stylet is inserted into the catheter body (before or after the catheter body has been inserted into the patient's body). The stylet is moved longitudinally within and with respect to the catheter body to bring about a desired deflection at the catheter distal end, as illustrated in FIGS. 7, 8, and 9, allowing the catheter to be negotiated through tortuous anatomy. Thereafter, the stylet is removed from the catheter. A guidewire may, thereafter, be inserted through the guide wire lumen to continue the procedure as is well known in the art.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An elongate member for shaping an ultrasound catheter for delivering ultrasonic energy to a treatment location within a patient's body, the catheter having proximal and distal ends, the distal end of the catheter having a distal passage aperture for the passage of a guide wire therethrough, the shaping member, comprising:

an elongate member having proximal and distal portions with a distal end having an outer diameter sufficiently larger than the distal passage aperture of the catheter to maintain the distal end of the shaping member within the catheter body at the distal end thereof during treatment.

2. The shaping member of claim 1 wherein at least a part of the elongate member distal portion is formed, at least in part, of radiopaque material.

3. The shaping member of claim 1 wherein the elongate member includes:

an elongate core member having proximal and distal portions with a distal end; and a flexible body having a distal end and disposed about a section of the elongate core member distal portion and being secured to the elongate core member at least a portion thereof.

4. The shaping member of claim 3 wherein the flexible body includes a plug at the distal end thereof having an outer diameter sufficiently larger than the distal aperture of the catheter to maintain the distal end of the shaping member within the catheter body at the distal end thereof during treatment.

5. The shaping member of claim 4 wherein the flexible body is formed, at least in part, of radiopaque material.

6. The shaping member of claim 5 wherein the radiopaque material comprises an alloy of platinum and nickel.

7. The shaping member of claim 6 wherein the platinum and nickel alloy comprises from about 88 to about 92 atomic percent platinum.

8. The shaping member of claim 4 wherein the elongate core member is formed, at least in part, of stainless steel.

9. The shaping member of claim 4 wherein the elongate core member distal portion is tapered in the distal direction.

10. The shaping member of claim 9 wherein the elongate core member includes a plurality of tapered regions at the distal portion thereof, the tapered regions tapering in the distal direction.

11. An elongate member for shaping an ultrasound catheter for delivering ultrasonic energy to a treatment location within a patient's body, the catheter having proximal and distal ends, the distal end of the catheter having a distal passage aperture for the passage of a guide wire therethrough, the elongate member, comprising:

an elongate member having proximal and distal portions and having a curve at a distal end thereof to bring about the desired deflection at the catheter distal end to negotiate the catheter through tortuous anatomy during treatment.

12. The shaping member of claim 11 wherein the curve is formed within up to about 2 mm of the elongate member distal end.

13. The shaping member of claim 12 wherein the curve is formed within up to about 1 mm of the elongate member distal end.

14. The shaping member of claim 11 wherein the elongate member includes:

an elongate core member having proximal and distal portions with a distal end; and a flexible body having a distal end and disposed about a section of the elongate core member distal portion and being secured to the elongate core member at least a part of the elongate core member distal section.

15. The shaping member of claim 14 wherein the flexible body is formed of a material having sufficient stiffness to bring about the desired curvature at the elongate member distal end.

16. An elongate member for shaping an ultrasound catheter for delivering ultrasonic energy to a treatment location within a patient's body, the catheter having proximal and distal ends, the distal end of the catheter having a distal passage aperture for the passage of a guide wire therethrough, the elongate member, comprising:

an elongate member having sufficient stiffness to bring about a desired deflection at the catheter distal end to negotiate the catheter through tortuous anatomy during treatment.

17. The shaping member of claim 16 wherein the elongate member is formed, at least in part, of stainless steel.

18. An ultrasonic catheter system, comprising:

an ultrasound delivery catheter comprising
an elongate body having proximal and distal portions,
a distal tip member mounted on a distal end of the catheter body and having at least one distal aperture therethrough;
at least one ultrasound transmission member extending longitudinally through at least a portion of the elongate body distal portion and configured to transmit ultrasonic vibration to the distal tip member; and
a shaping elongate member extending longitudinally through at least the distal portion of the catheter body and having an outer diameter at a distal end thereof sufficiently larger than the distal aperture of the distal tip member to maintain the distal end of the shaping member within the catheter body at the catheter distal end during treatment.

19. The catheter system of claim 18 wherein the shaping member has sufficient stiffness to bring about a desired deflection at the catheter distal end to negotiate the catheter through tortuous anatomy during treatment.

20. The catheter system of claim 19 wherein the shaping member has a predetermined curve at the distal end thereof.

21. A method for shaping an ultrasound catheter for delivering ultrasonic energy to a treatment location within a patient's body, method comprising:

advancing a catheter system through the patient's body, the system comprising:
an ultrasound delivery catheter comprising
an elongate body having proximal and distal portions,
a distal tip member mounted on a distal end of the catheter body and having at least one distal aperture therethrough;
at least one ultrasound transmission member extending longitudinally through at least a portion of the elongate body distal portion and configured to transmit ultrasonic vibration to the distal tip member; and
a shaping elongate member extending longitudinally through at least the distal portion of the catheter body and having a predetermined shape at a distal end thereof, the shaping member distal end having an outer diameter sufficiently larger than the distal aperture of the distal tip member to maintain the shaping member distal end within the catheter body during treatment, the shaping member having sufficient stiffness to bring about a desired deflection at the catheter distal end to negotiate the catheter through tortuous anatomy during treatment;
moving the shaping member within the catheter body longitudinally with respect to the catheter body to bring about a desired deflection at the catheter distal end to negotiate the catheter through tortuous anatomy;
advancing the catheter system within the anatomy to reach a desire area within the anatomy; and
removing the shaping member from the catheter body.

* * * * *

UNITED STATES PATENT AND TRADEMARK OFFICE
CERTIFICATE OF CORRECTION

PATENT NO. : 6,423,026 B1
DATED : July 23, 2002
INVENTOR(S) : Douglas H. Gesswein et al.

It is certified that error appears in the above-identified patent and that said Letters Patent is hereby corrected as shown below:

<u>Title page,</u>
Item [57], ABSTRACT,
Line 1, change "style", to read -- stylet --.

<u>Column 4,</u>
Line 33, delete "=" and start a new paragraph with the sentence "The coil 92. . .".

Signed and Sealed this

Twenty-first Day of January, 2003

JAMES E. ROGAN
*Director of the United States Patent and Trademark Office*